(12) United States Patent
de Graaf et al.

(10) Patent No.: US 12,714,812 B2
(45) Date of Patent: Aug. 25, 2026

(54) VENTILATOR SYSTEM

(71) Applicant: KONINKLIJKE PHILIPS N.V., Eindhoven (NL)

(72) Inventors: Pascal de Graaf, Eindhoven (NL); Samer Bou Jawde, Cambridge, MA (US); Harold Johannes Antonius Brans, Eindhoven (NL); Robert William Murdoch, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 980 days.

(21) Appl. No.: 17/969,958

(22) Filed: Oct. 20, 2022

(65) Prior Publication Data

US 2023/0191055 A1 Jun. 22, 2023

Related U.S. Application Data

(60) Provisional application No. 63/290,583, filed on Dec. 16, 2021.

(51) Int. Cl.

| | |
|---|---|
| ***A61M 16/00*** | (2006.01) |
| ***A61M 16/04*** | (2006.01) |
| ***A61M 16/06*** | (2006.01) |

(52) U.S. Cl.

CPC ........ *A61M 16/024* (2017.08); *A61M 16/049* (2014.02); *A61M 16/0672* (2014.02);

(Continued)

(58) Field of Classification Search

CPC .............. A61M 16/06; A61M 16/0666; A61M 16/0672; A61M 16/049; A61M 16/0488;

(Continued)

(56) References Cited

U.S. PATENT DOCUMENTS 4,533,137 A * 8/1985 Sonne .................... A63B 23/18 482/13
6,631,716 B1 * 10/2003 Robinson ............. A61M 16/20 482/13

(Continued)

FOREIGN PATENT DOCUMENTS

EP 2514470 A1 10/2012
WO 2021206628 A1 1/2021

OTHER PUBLICATIONS

Onodera, Y. et al., (2018). "A high-flow nasal cannula system with relatively low flow effectively washes out CO 2 from the anatomical dead space in a sophisticated respiratory model made by a 3D printer." Intensive care medicine experimental, 6(1), 1-9.

(Continued)

*Primary Examiner* — Douglas Y Sul
(74) *Attorney, Agent, or Firm* — Daniel H. Brean

(57) ABSTRACT

According to an aspect, there is provided a ventilator system. The ventilator system comprises: a mouthpiece, to be received within a user's mouth, wherein the mouthpiece comprises: a passage for permitting a flow of gases through the mouthpiece between a first side of the passage to be inside the user's mouth and a second side of the passage to be outside the user's mouth; a passage adjustment component for selectively adjusting a flow area of the passage; and one or more sensors mounted on the mouthpiece, wherein the sensors comprise a pressure sensor configured to measure a pressure at the first side of the passage; and a controller configured to control: a flow rate and/or concentration of oxygen supplied to the user through a nasal cannula; a total flow rate of air and oxygen supplied through the nasal cannula; and/or the flow area of the passage, based on the pressure measured by the pressure sensor.

13 Claims, 4 Drawing Sheets

(52) U.S. Cl.
CPC ............... *A61M 2205/3368* (2013.01); *A61M 2230/205* (2013.01); *A61M 2230/432* (2013.01)

(58) Field of Classification Search
CPC .............. A61M 16/024; A61M 16/022; A61M 2016/103; A61M 2230/00
See application file for complete search history.

(56) References Cited

U.S. PATENT DOCUMENTS

| | | | | |
|---|---|---|---|---|
| 8,844,530 | B2 | 9/2014 | Birnkrant | |
| 9,364,623 | B2 * | 6/2016 | Lellouche | A61M 16/026 |
| 10,376,410 | B2 | 8/2019 | Flanagan | |
| 10,610,731 | B2 * | 4/2020 | Lyapko | A63B 23/18 |
| 2005/0034724 | A1 | 2/2005 | O'Dea | |
| 2007/0277826 | A1 | 12/2007 | Lurie | |
| 2011/0124470 | A1 | 5/2011 | Spurling | |
| 2015/0101610 | A1 | 4/2015 | Nitta | |
| 2016/0058346 | A1 * | 3/2016 | Heinonen | A61B 5/14542 600/301 |
| 2016/0184541 | A1 * | 6/2016 | Laksov | G16H 40/63 128/204.23 |
| 2016/0296721 | A1 | 10/2016 | Landis | |
| 2016/0367779 | A1 | 12/2016 | Landis | |
| 2017/0319129 | A1 * | 11/2017 | Shah | A61N 1/0548 |
| 2018/0071469 | A1 | 3/2018 | Oldfield | |
| 2018/0078726 | A1 | 3/2018 | Barraclough | |
| 2018/0085544 | A1 * | 3/2018 | Holyoake | A61M 16/0078 |
| 2019/0217155 | A1 | 7/2019 | Boutros | |
| 2022/0313929 | A1 * | 10/2022 | Beck | A61M 16/205 |
| 2022/0379066 | A1 | 12/2022 | Navarro | |
| 2022/0395653 | A1 * | 12/2022 | Chapman | G16H 20/10 |

OTHER PUBLICATIONS

Ritchie, J.E. et al., (2011). "Evaluation of a humidified nasal high-flow oxygen system, using oxygraphy, capnography and measurement of upper airway pressures." Anaesthesia and intensive care, 39(6), 1103-1110.

Parke, R. et al., (2009). "Nasal high-flow therapy delivers low level positive airway pressure." British journal of anaesthesia, 103(6), 886-890.

https://expand-a-lung.com/.

International Search Report for PCT/EP2022/084326 filed on Dec. 5, 2022.

* cited by examiner 200
224
220
226
210, 212
222
214a
214b
202a
210, 216
202
202b
218a
210, 214
204
228
218b
210, 218

T0
T1
T2
T3
T4
T5
T6
T7
T8
PEEP
SpO2
PaCO2
Flow
Total flow
Air flow
Oxygen flow
Mouthpiece orifice
Time

VENTILATOR SYSTEM

CROSS-REFERENCE TO RELATED APPLICATIONS

This patent application claims the priority benefit under 35 U.S.C. § 119(e) of U.S. Provisional Application No. 63/290,583, filed on Dec. 16, 2021, the contents of which are herein incorporated by reference.

FIELD OF THE INVENTION

The present disclosure relates to a ventilator system and is particularly, although not exclusively, concerned with a High Flow Nasal Therapy (HFNT) system with improved pressure control.

BACKGROUND OF THE INVENTION

Ventilator systems, such as High Flow Nasal Therapy (HFNT) ventilator systems can be used to improve oxygenation of a user by introducing flows of oxygen rich air through a loose-fitting nasal cannula.

A secondary effect of HFNT is that an increased level of expiratory pressure, such as a Positive End-Expiratory Pressure (PEEP) is created, which helps to increase removal of carbon dioxide from the user's airways and/or blood. Utilising the PEEP effect of HFNT could enable such ventilator systems to be used as an alternative to pressure support devices, such as Continuous Positive Airway Pressure (CPAP) and Biphasic Positive Airway Pressure (BiPAP) systems and other non-invasive ventilator systems.

However, the lack of control over the level of expiratory pressure achieved by HFNT systems is currently limiting this use. In particular, when the user opens their mouth, the positive pressure is effectively lost. This complicates the task of accurately setting and controlling the PEEP, especially at night whilst the user is asleep.

SUMMARY OF THE INVENTION

According to an aspect of the present disclosure, there is provided ventilator system, such as a High Flow Nasal Therapy, HFNT, system, comprising:

a mouthpiece, to be received within a user's mouth, wherein the mouthpiece comprises:

a passage for permitting a flow of gases through the mouthpiece between a first side of the passage to be inside the user's mouth and a second side of the passage to be outside the user's mouth;

a passage adjustment component for selectively adjusting a flow area of the passage; and one or more sensors mounted on the mouthpiece, wherein the sensors comprise a pressure sensor configured to measure a pressure at the first side of the passage; and a controller configured to control:

a flow rate and/or concentration of oxygen supplied to the user through a nasal cannula;

a total flow rate of air and oxygen supplied through the nasal cannula; and/or the flow area of the passage, based on the pressure measured by the pressure sensor.

The controller may be configured to determine a Positive End-Expiratory Pressure, PEEP, based on one or more pressure measurements from the pressure sensor. The controller may be configured to control: the flow rate and/or concentration of oxygen supplied through the nasal cannula; the total flow rate of air and oxygen supplied through the nasal cannula; and/or the flow area of the passage, based on the determined PEEP.

The ventilator system may further comprise the nasal cannula for supplying a flow of air and/or oxygen to one or both nares of the user. Additionally or alternatively, the ventilator system may further comprise:

an air and/or oxygen supplying apparatus configured to supply flows of air and/or oxygen to the nasal cannula. Flow rates and/or concentrations of the air and oxygen supplied by air and/or oxygen supplying apparatus may be controllable.

The ventilator system may further comprise an oxygen saturation sensor configured to determine oxygen saturation of the user. For example, the oxygen saturation sensor may comprise one or more light-emitting diodes arranged to face a photodiode through a translucent part of the user's body. Additionally or alternatively, the controller may be configured to receive an oxygen saturation measurement. The controller may be configured to control: the flow rate and/or concentration of oxygen supplied through the nasal cannula; the total flow rate of air and oxygen supplied through the nasal cannula; and/or the flow area of the passage, based on the oxygen saturation. The oxygen saturation sensor may be mounted on the mouthpiece or on the nasal cannula.

The sensors may comprise a temperature sensor configured to measure a temperature of gases passing through the passage. The temperature sensor may be configured to measure the temperature of the gases repeatedly with a predetermined frequency. In this way, the temperature sensor may be configured to measure a temperature of gasses when the user is exhaling and when the user is not exhaling. The controller may be configured to control: a flow rate and/or concentration of oxygen supplied through the nasal cannula; a total flow rate of air and oxygen supplied through the nasal cannula; and/or the flow area of the passage, based on the measured temperature.

The sensors may comprise a capnogram configured to measure a partial pressure of carbon dioxide in gases passing through the passage. For example, the capnogram may comprise a source of infrared, such as an infrared light-emitting diode, arranged to pass infrared light through the gases passing through the passage, and an infrared sensor for measuring infrared light and determining a power of infrared light absorbed by the gases. The controller is configured to determine an end tidal carbon dioxide measurement based on measurements from the capnogram. Alternatively, the controller may be configured to receive an end tidal carbon dioxide measurement. The controller may be configured to control: a flow rate and/or concentration of oxygen supplied through the nasal cannula; a total flow rate of air and oxygen supplied through the nasal cannula; and/or the flow area of the passage, based on the measurement from the capnogram, such as the partial pressure of carbon dioxide and/or the end tidal carbon dioxide measurement, and/or based on the received end tidal carbon dioxide measurement.

The controller may be configured to determine a partial pressure of carbon dioxide within arterial blood of the user based on measurements from the capnogram. Alternatively, the controller may be configured to receive a determined partial pressure of carbon dioxide within arterial blood. The controller may be configured to control: a flow rate and/or concentration of oxygen supplied through the nasal cannula; a total flow rate of air and oxygen supplied through the nasal cannula; and/or the flow area of the passage, based on the determined partial pressure of carbon dioxide within the arterial blood.

The ventilator system may comprise a user input device. The controller may be configured to receive one or more input control parameters from the user or another user via the user input device. The controller may be configured to control: a flow rate and/or concentration of oxygen supplied through the nasal cannula; a total flow rate of air and oxygen supplied through the nasal cannula; and/or the flow area of the passage, based on the one or more input control parameters. The input control parameters may comprise: a target pressure, e.g. PEEP value, a target oxygen saturation value and/or a target value of partial pressure of carbon dioxide, e.g. partial pressure of carbon dioxide within the arterial blood of the user.

The controller may be configured to monitor measurements from the one or more sensors mounted on the mouthpiece. The controller may be further configured to control: a flow rate and/or concentration of oxygen supplied through the nasal cannula; a total flow rate of air and oxygen supplied through the nasal cannula; and/or the flow area of the passage, in order to maintain determined values of pressure, oxygen saturation and/or partial pressure of carbon dioxide within respective desirable ranges, e.g. within ranges greater than or equal to, less than or equal to, and/or within ranges defined by predetermined threshold differences from the respective target values. The desirable ranges may be determined based on respective target values defined by the input control parameters.

According to another aspect of the present disclosure, there is provided a mouthpiece for the above-mentioned ventilator system, wherein the mouthpiece is to be received within the user's mouth, wherein the mouthpiece comprises: a passage for permitting a flow of gases through the mouthpiece between a first side of the passage to be inside the user's mouth and a second side of the passage to be outside the user's mouth; a passage adjustment component for selectively adjusting a flow area of the passage; and one or more sensors mounted on the mouthpiece, wherein the sensors comprise a pressure sensor configured to measure a pressure at the first side of the passage.

According to another aspect of the present disclosure, there is provided a method of operating a ventilator system, wherein the ventilator system comprises: a nasal cannula for supplying a flow of air and/or oxygen to one or both nares of a user; a mouthpiece, to be received within the user's mouth, wherein the mouthpiece comprises: a passage for permitting a flow of gases through the mouthpiece between a first side of the passage to be inside the user's mouth and a second side of the passage to be outside the user's mouth; a passage adjustment component for selectively adjusting a flow area of the passage; and one or more sensors mounted on the mouthpiece, wherein the sensors comprise a pressure sensor configured to measure a pressure at the first side of the passage; and a controller configured to control the operation of the ventilator system, wherein the method comprises: determining a pressure measurement from the pressure sensor; and, based on the determined pressure measurement: controlling a flow rate and/or concentration of oxygen supplied through the nasal cannula; controlling a total flow rate of air and oxygen supplied through the nasal cannula; and/or controlling the flow area of the passage.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figures 1, 2A:
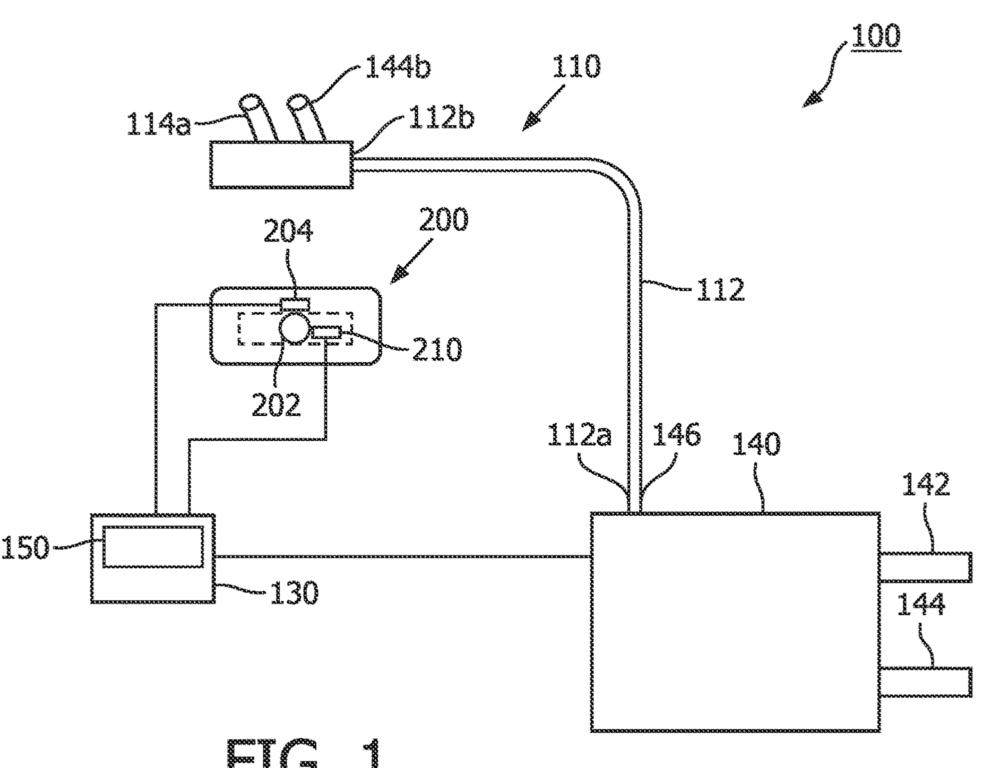
FIG. 1 is a schematic view of a ventilator system according to arrangements of the present disclosure.
FIGS. 2*a* and 2*b* are schematic views of a mouthpiece for the ventilator system depicted in FIG. 1, with a passage through mouthpiece in open and partially occluded conditions respectively.

With reference to FIG. 1, a ventilator system 100, such as a High Flow Nasal Therapy (HFNT) system, according to arrangements of the present disclosure comprises a nasal cannula 110, for supplying a flow of air and/or oxygen to one or both nares of a user, a mouthpiece 200, to be received within the user's mouth, and a controller 130 for controlling the operation of the ventilator system 100.

The ventilator system 100 may further comprise an air and/or oxygen supplying apparatus 140 configured to supply flows of air and/or oxygen to the nasal cannula 110. The air and/or oxygen supplying apparatus 140 may have a first inlet 142 configured to be coupled to a supply of air, e.g. high pressure air, such as a high pressure airline, e.g. provided at a hospital or other facility in which the ventilator system 100 is to be used, a cylinder containing pressurised air, or a mechanical flow generator.

The air and/or oxygen supplying apparatus 140 further comprises a second inlet 144 to be coupled to a supply of oxygen, e.g. high pressure oxygen, such as a high pressure oxygen-line, e.g. provided at a hospital or other facility in which the ventilator system 100 is to be used, a cylinder containing pressurised oxygen, or an oxygen concentrator.

The air and/or oxygen supplying apparatus 140 further comprises an outlet 146 to be coupled to the nasal cannula 110. The air and/or oxygen supplying apparatus is configured to blend the air and oxygen received at the first and second inlets 142, 144, e.g. by adjusting the relative flow rate of air and oxygen output via the outlet 146, and supply the blended air and/or oxygen to the nasal cannula 110 via the outlet 146. The flow rates and/or concentrations of the air and oxygen supplied by the air and/or oxygen supplying apparatus may be controllable, e.g. by the controller 130.

The air and/or oxygen supplying apparatus 140 may be configured to adjust a temperature and/or humidity of the air and/or oxygen supplied to the nasal cannula 110, in order to improve the comfort of the user.

As depicted, the nasal cannula 110 may comprise a tube 112 coupled to the air and/or oxygen supplying apparatus 140 at a first end 112*a* of the tube. At a second end 112*b*, the tube 112 may be divided into two prongs 114*a*, 114*b* to be received within the nares of the user, so that the supply of air and/or oxygen can flow into the user's nose. The prongs 114*a*, 114*b* may be configured to engage the inside of the user's nares in order to create a seal between the prongs and the user's nares to prevent or reduce leakage of the supplied air and/or oxygen out of the user's nose.

As described in more detail below, the mouthpiece 200 comprises a passage 202 for permitting a flow of gases, such as air and/or oxygen from the nasal cannula that is not inhaled and exhaled gases, to pass through the mouthpiece 200 between a first side 202*a* of the passage the inside of the user's mouth and a second side 202*b* of the passage outside of the user's mouth when the mouthpiece is received within the user's mouth during use of the ventilator system 100. The mouthpiece 200 further comprises a passage adjustment component 204 for selectively adjusting a flow area through the passage 202.

The mouthpiece 200 further comprises one or more sensors 210 mounted on the mouthpiece. The sensors may comprise a pressure sensor 212 configured to measure a pressure at the first side of the passage or within the passage 202. The pressure sensors 212 may thereby be configured to measure a pressure of air and other gases within the user's airway, e.g. within the user's mouth. The controller 130 may be configured to determine a Positive End-Expiratory Pressure (PEEP) of the user based on one or more pressure measurement made by the pressure sensor 212.

As described in more detail below, the controller 130 is further configured to control the operation of the ventilator system 100 based on measurements from the one or more sensors 210, such as based on pressure, e.g. the determined PEEP. The controller 130 may control a flow rate and/or concentration of oxygen supplied through the nasal cannula 110 based on measurements from the one or more sensors 210. For example, the controller 130 may control the operation of the air and/or oxygen supplying apparatus 140 in order to control the flow rate and/or concentration of oxygen supplied to the nasal cannula 110. Additionally or alternatively, the controller 130 may control the total flow rate of air and oxygen suppled though the nasal cannula 110 based on the measurements from the one or more sensors 210. For example, the controller 130 may control the operation of the air and/or oxygen supplying apparatus 140 in order to control the total flow rate of air and oxygen suppled to the nasal cannula 110. The controller 130 may be further configured to control the passage adjustment component 204 to selectively adjust the flow area of the passage 202 based on the measurements from the one or more sensors 210, e.g. based on the pressured pressure or determined PEEP.

Figure 3:
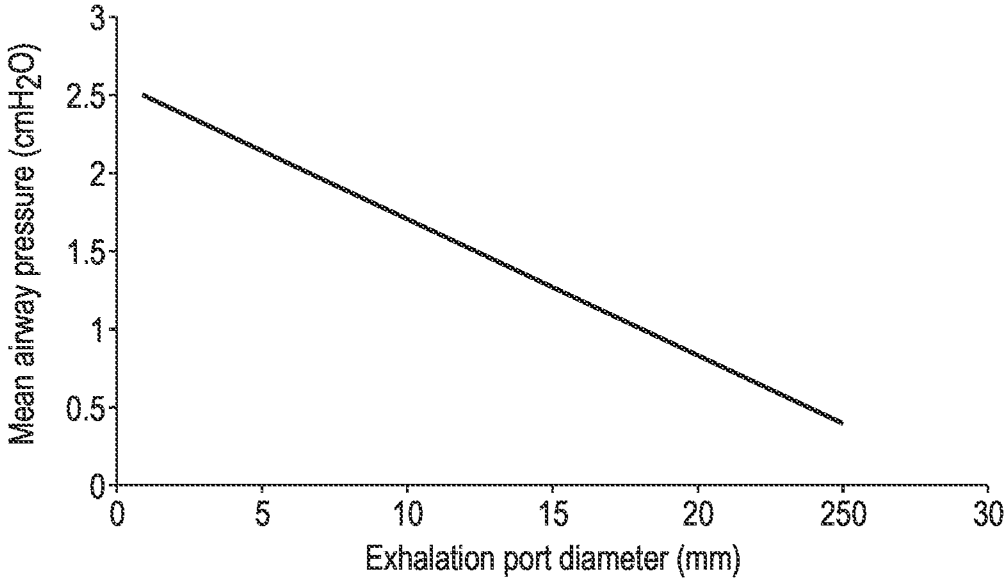
FIG. 3 is a graph illustrating the effect of different exhalation passage areas on mean airway pressure.

FIG. 3 illustrates the relationship between diameter of the passage and mean airway pressure of a user. As can be seen in FIG. 3, mean airway pressure of the user increases as diameter of the passage decreased. For example, mean air pressure may be inversely proportion to the diameter of the passage.

In the arrangement shown in FIG. 1, the controller 130 is separate from the mouthpiece 200, nasal cannula 110 and the air and/or oxygen supplying apparatus 140. However, in other arrangements, the controller 130, or modules of the controller 130, may be integrated into the mouthpiece 200, nasal cannula 110 and/or the air and/or oxygen supplying apparatus 140. For example, a plurality of circuits for performing the functions of the controller 130 described herein may be integrated into the mouthpiece 200, nasal cannula 110 and/or the air and/or oxygen supplying apparatus 140.

Figure 2B:
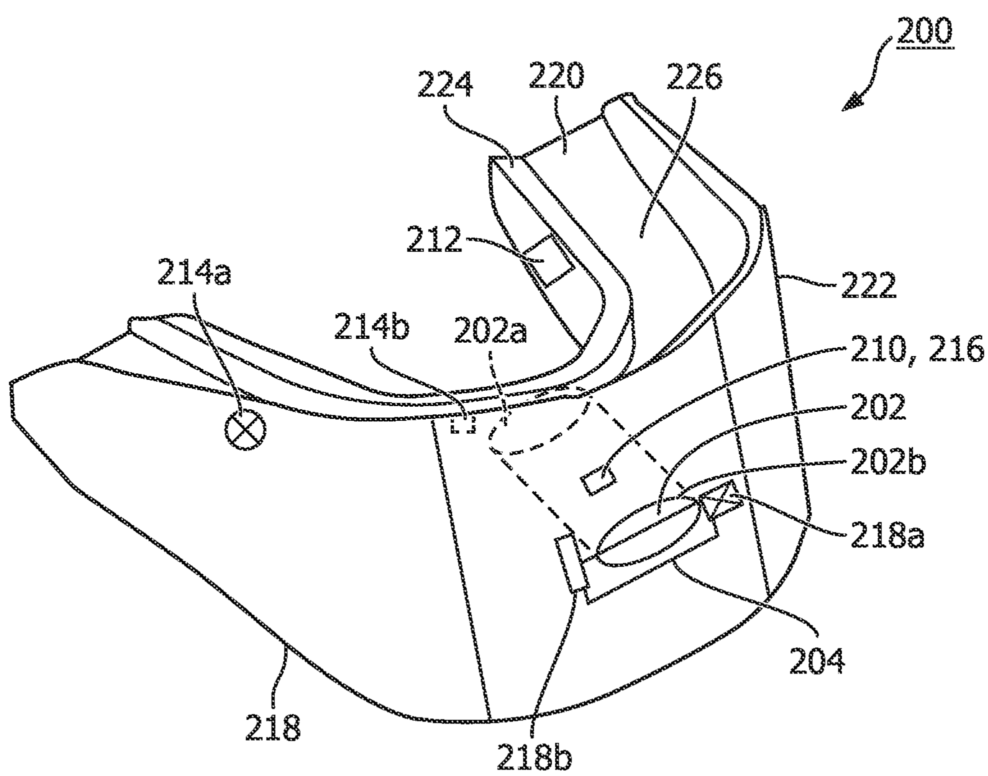

With reference to FIGS. 2*a* and 2*b*, collectively referred to as FIG. 2, the mouthpiece 200 may comprises a body part 220 to be received between the upper and lower teeth of the user. The mouthpiece 200 may further comprise an outer wall 222 extending at least partially around an outer periphery of the body part 220. The outer wall 222 may projected upwardly relative to the body part 220 and may be shaped so that at least a portion of the outer wall 222 is positioned between the user's teeth and upper lip when the mouthpiece 200 is received within the user's mouth. The mouthpiece 200 may further comprise in inner wall 224 extending at least partially around an inner periphery of the body part 220. The inner wall 224 may similarly project upwardly relative to the body part 220, so that the inner and outer walls 222, 224 together form an upper channel 226 between them, in which the user's upper teeth are received when the mouthpiece 200 is installed within the user's mouth. A bottom of the upper channel 226 may be formed by the body part 220. In some arrangements, the outer wall 222 may additionally or alternatively project downwards relative to the body part 220, and may be shaped so that at least a portion of the outer wall is positioned between the user's lower teeth and lower lip when the mouthpiece 200 is received within the user's mouth. In such arrangements, the inner wall 224 may similarly project downwards relative to the body portion in order to create a lower channel 228 for receiving the user's bottom teeth when the mouthpiece 200 is installed within the user's mouth.

As depicted in FIG. 2, the passage 202 may be formed in the body part 220 and optionally the inner and/or outer walls 222, 224. The mouthpiece 200, e.g. the body part 220, may be sized and shaped so that when the mouthpiece is installed within the user's mouth and the user's mouth is closed, the passage 202 is substantially uncovered by the user's lips. In this way, the mouthpiece 200 may ensure that the user's is able to exhale, and optionally inhale, through the passage 202 whilst their mouth is closed when the mouthpiece 200 is installed.

In other arrangements, the mouthpiece 200 may be shaped in any other way such that the passage 202 is arranged to permit a flow of gases through the mouthpiece between the inside of the user's mouth and outside the user's mouth, and so that the user's mouth is otherwise substantially sealed when the mouthpiece is installed and, optionally, the user's mouth is closed.

As depicted in FIG. 2, the passage adjustment component 204 may comprise a moveable element mounted on the mouthpiece 200, which is configured to be selectively moved relative to the passage 202 in order to at least partially occlude the passage and thereby adjust a flow area through the passage. In the arrangement shown in FIG. 2*b*, the moveable element 204 has been moved such that the movable element is at least partially disposed within the passage 202, or over an opening into the passage 202, in order to reduce the flow area though the passage.

In other arrangements, the movable element 204 may be coupled to or configured to engage a wall of the passage 202 such that movement of the movable element can displace the wall of the passage and thereby adjust the flow area through the passage, e.g. by collapsing or opening the passage. The mouthpiece, e.g. the body part 220, may comprise a resilient material and may be configured such that the passage 202 is biased into an open configuration when the wall is not being displaced by the movable element 204. In other arrangements, the passage adjustment component 204 may be configured in any other way in order to permit the flow area of the passage to be selectively adjusted.

The ventilator system 100 may further comprise an oxygen saturation sensor 214. The oxygen saturation sensor may be configured to measure an oxygen saturation ($SpO_2$) of a user of the ventilator system 100. As depicted in FIG. 2, the oxygen saturation sensor 214 may be mounted on the mouthpiece 200. In other words, the oxygen saturation sensor 214 may be one of the sensors 210 mentioned above.

In the arrangement shown, the oxygen saturation sensor 214 comprises two or more light-emitting diodes 214*a* configured to emit light of two or more difference wavelengths. The two or more light-emitting diodes are arranged to face a photodiode 214*b* through a translucent part of the user's body, such as part of the user's upper or lower lip, when the ventilator system 100 is in use. The oxygen saturation sensor 214 may be configured to determine the oxygen saturation based on differences in the absorption of the different wavelengths of light.

In other arrangements, the oxygen saturation sensor 214 may be integrated into the nasal cannula 110. For example, the light emitting diodes 214*a* of the oxygen saturation sensor may be arranged to pass light through user's skin around the user's nose, such as through one of the user's alae, to reach the photodiode 214*b*.

In still further arrangements, the oxygen saturation sensor 214 may be separate from the mouthpiece and the nasal cannula. For example, the oxygen saturation sensor 214 may comprise an oximeter to be attached to the user's finger or ear. In such arrangements, the oxygen saturation sensor 214 may be part of, or may be separate from, the ventilator system 100.

The controller 130 may be configured to receive a measurement of an oxygen saturation, e.g. from the oxygen saturation sensor 214, and control the operation of the ventilator system 100 based on the oxygen saturation. In particular, the controller 130 may be configured to control the flow rate and/or concentration of oxygen supplied through the nasal cannula 110, the total flow rate of air and oxygen supplied through the nasal cannula and/or the flow area of the passage 202, based on the received measurement of oxygen saturation.

The ventilator system 100 may further comprise one or more temperature sensors 216 configured to measure a temperature of gases passing through the passage 202. As depicted in FIG. 2, one or more of the temperature sensors 216 may be mounted on the mouthpiece 200. In other words, one or more of the temperature sensor 216 may be ones of the sensors 210.

The one or more temperature sensors 216 may be configured to measure the temperature of the gases passing through the passage 202 repeatedly with a predetermined frequency. For example, the temperature sensors 216 may be configured to measure the temperature of the gases once per second or twice per second. In this way, the temperature sensor may be configured to measure the temperature of gases when the user is exhaling and when the user is not exhaling, e.g. when the user is inhaling.

When the user is not exhaling, the gases passing through the passage 202 may be gases that have been delivered through the nasal cannula 110. When the user is exhaling, the gases passing through the passage 202 may include exhaled gases from the user's lungs and airways. The exhaled gases may have a different, e.g. higher, temperature from the gases introduced though the nasal cannula 110.

The controller 130 may be configured to determine when the user is inhaling and when the user is exhaling based on the temperature measurements from the one or more temperature sensors 216. The controller 130 may be configured to control the operation of the ventilator system 100 based on the temperature measured by the temperature sensor 216, or the determination when the user is inhaling and exhaling. In particular, the controller 130 may be configured to control the flow rate and/or concentration of oxygen supplied through the nasal cannula, the total flow rate of air and oxygen supplied through the nasal cannula and/or the passage adjustment component to selectively adjust the area of the passage, based on the temperature of gases passing through the passage. For example, when the user is inhaling and/or the temperature is at or below a threshold value, the flow rate and concentration of oxygen supplied through the nasal cannula and, optionally, the total flow rate of air and oxygen supplied through the nasal cannula may be greater than when the user is exhaling, or the temperature is below the threshold value, or another threshold value.

The ventilator system 100 may further comprise a capnogram 218 configured to measure a partial pressure of carbon dioxide in gases passing through the passage 202. The capnogram 218 may be mounted on the mouthpiece 200. In other words, the capnogram 218 may be one of the sensors 210 mentioned above. As depicted in FIG. 2, the capnogram 218 may comprise a source of infrared light, such as an infrared light-emitting diode 218*a*, arranged to pass infrared light through the gases passing through the passage 202, and an infrared sensor 218*d*, such as a photodiode, for measuring infrared light and determining a power of infrared light absorbed by the gases. The capnogram 218 may be configured to determine the partial pressure of carbon dioxide within the gases based on the power of infrared light absorbed by the gases.

The controller 130 may be configured to determine an end tidal carbon dioxide measurement based on measurements from the capnogram 218, e.g. based on the partial pressure of carbon dioxide within the gases.

The controller 130 may be configured to control the operation of the ventilator system 100 based on the measured partial pressure of carbon dioxide in gases passing through the passage 202 and/or the end tidal carbon dioxide measurement. In particular, the controller may be configured to control the flow rate and/or concentration of oxygen supplied through the nasal cannula 110, the total flow rate of air and oxygen supplied through the nasal cannula and/or the passage adjustment component 204 to selectively adjust the flow area of the passage 202, based on the measured partial pressure of carbon dioxide in gases passing through the passage 202 and/or the end tidal carbon dioxide measurement.

Additionally or alternatively, the controller 130 may be configured to determine, e.g. estimate, a partial pressure of carbon dioxide within arterial blood of the user based on one or more measurements from the capnogram, or receive a determination of a partial pressure of carbon dioxide within arterial blood. In such arrangements, the controller 130 may be configured to control the operation of the ventilator system 100 based on the partial pressure of carbon dioxide within arterial blood. In particular, the controller may be configured to control the flow rate and/or concentration of oxygen supplied through the nasal cannula 110, the total flow rate of air and oxygen supplied through the nasal cannula and/or the passage adjustment component to selectively adjust the area of the passage, based on the partial pressure of carbon dioxide within arterial blood.

In other arrangements, the controller 130 may be configured to receive a measurement of partial pressure of carbon dioxide, e.g. within arterial blood. For example, the controller may receive the measurement of partial pressure of carbon dioxide from a transcutaneous sensor, which may be included in or separate from the ventilator system 100. The controller 130 may be configured to control the operation of the ventilator system 100 based on the received partial pressure measurement. In particular, the controller may be configured to control the flow rate and/or concentration of oxygen supplied through the nasal cannula 110, the total flow rate of air and oxygen supplied through the nasal cannula and/or the passage adjustment component to selectively adjust the area of the passage, based on the received partial pressure measurement.

The ventilator system 100 may further comprise a user input device 150, such as one or more switches, buttons, a touch screen, or any other device for receiving an input from the user or another user. As depicted in FIG. 1, the user input device 150 may be provided on the controller 130. In other arrangements, the user input device 150 may be provided on any other component of the ventilator system 100. In some arrangements, the user input device 150 may be provided on a separate computing device, e.g. a portable computing device, such as a tablet computer or smartphone.

The controller 130 may be configured to receive one or more input control parameters from the user or another user via the user input device 150. For example, the input control parameters may comprise a target pressure, e.g. PEEP, value, a target oxygen saturation value and/or a target value of partial pressure of carbon dioxide within arterial blood. The controller 130 may be configured to control the operation of the ventilator system 100 based on one or more of the target values input via the user input device. In particular, the controller may be configured to control the flow rate and/or concentration of oxygen supplied through the nasal cannula 110, the total flow rate of air and oxygen supplied through the nasal cannula and/or the passage adjustment component to selectively adjust the area of the passage, based on the target values.

In one or more arrangements, the controller 130 may be configured to monitor measurements from the one or more sensors 210 and control the operation of the ventilator system 100 in order to maintain received and/or determined values of pressure, e.g. PEEP, oxygen saturation and/or partial pressure of carbon dioxide within arterial blood of the user at or close to the respective target values. The controller 130 may be configured to determine desirable ranges of the pressure, e.g. PEEP, oxygen saturation and/or partial pressure of carbon dioxide within arterial blood based on the target values. For example, the desirable ranges may be ranges greater than and optionally equal to, less than and optionally equal to, or within a threshold difference of the target value. The controller 130 may be configured to monitor measurements from the one or more sensors 210 and control the operation of the ventilator system 100 in order to maintain received and/or determined values of pressure, e.g. PEEP, oxygen saturation and/or partial pressure of carbon dioxide within arterial blood within the respective desirable ranges. The controller 130 may be configured to control the flow rate and/or concentration of oxygen supplied through the nasal cannula, the total flow rate of air or oxygen supplied through the nasal cannula and/or the passage adjustment component to selectively adjust the area of the passage in order to maintain received and/or determined values of pressure, e.g. PEEP, oxygen saturation and/or partial pressure of carbon dioxide within arterial blood within the respective desirable ranges.

Figure 4:
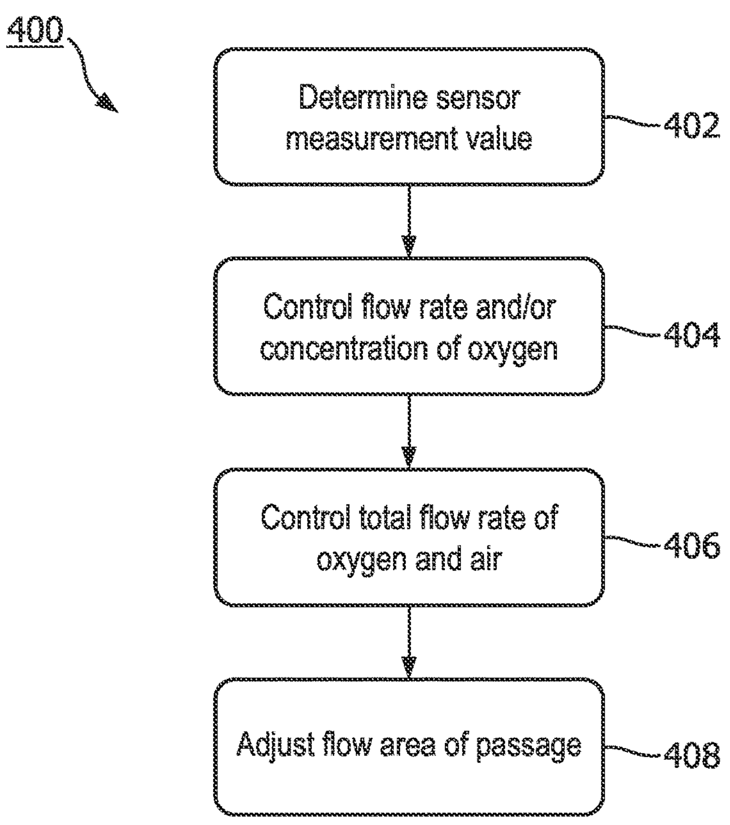
FIG. 4 is a flow diagram illustrating a method of operating the ventilator system shown in FIG. 1, according to arrangements of the present disclosure.

With reference to FIG. 4, a method 400 of operating a ventilator system, such as the ventilator system 100 comprises a first step 402, in which a sensor measurement value is determined, e.g. from a sensor of the ventilator system, such as one of the sensors 210 mounted on the mouthpiece. For example, in the first step a pressure at the first side 202*a* of the passage 202, e.g. a PEEP of the user, may be determined based on a pressure measurement from the pressure sensor 212 mounted on the mouthpiece 200. Additionally or alternatively, in the first step 402, an oxygen saturation of the user, an end tidal carbon dioxide measurement of the user and/or a partial pressure of carbon dioxide within arterial blood of the user may be determined or received by a controller performing the method 400.

The method 400 further comprises a second step 404, in which a flow rate and/or concentration of oxygen supplied through the nasal cannula of the ventilator system is controlled based on the sensor measurement value, such as the pressure, e.g. PEEP, oxygen saturation, end tidal carbon dioxide measurement and/or partial pressure of carbon dioxide within arterial blood.

Additionally or alternatively, the method may comprise a third step 406, in which a total flow rate of air and oxygen supplied through the nasal cannula is controlled based on the sensor measurement value.

Additionally or alternatively again, the method 400 may comprise a fourth step 408, in which the flow area of the passage is adjusted based on the sensor measurement value, e.g. by controlling the operation of the passage adjustment component.

Figure 5:
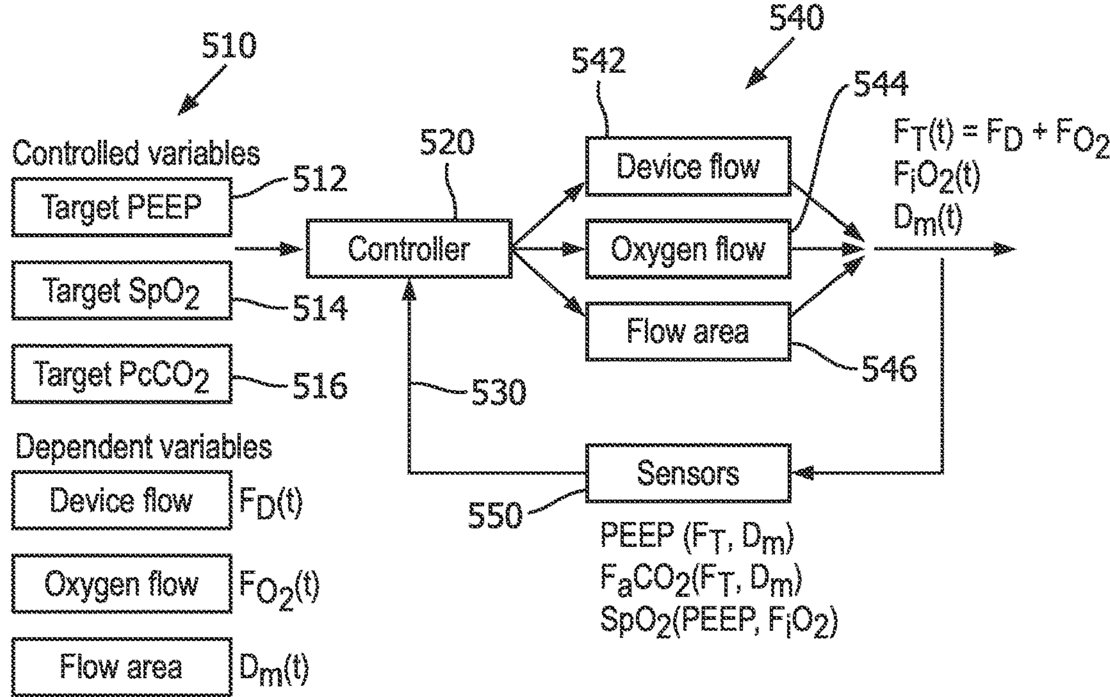
FIG. 5 is a flow diagram illustrating another method of operating the ventilator system, according to arrangements of the present disclosure.

FIG. 5 is a flow chart illustrating the operation of one arrangement of the ventilator system 100 described above. FIG. 5 illustrates the input of target values 510, such as target values of pressure, e.g. PEEP 512, oxygen saturation ($SpO_2$) 514 and partial pressure of carbon dioxide ($PaCO_2$) 516, e.g. with the user's blood. The input target values 510 may be received from a user input device, such as the user input device 150. FIG. 5 illustrates a control block 520 illustrating processing of the input target values and sensor measurements 530, e.g. by the controller 130 of the ventilator system. FIG. 5 further illustrates output control parameters 540 of the controller 130 for controlling the operation of the ventilator system. In the arrangement shown in FIG. 5, the output control parameters 540 comprise total flow rate of air and oxygen 542 supplied to the nasal cannula, flow rate of oxygen 544 supplied to the nasal cannula and flow area 546 of the passage 202 in the mouthpiece. At a sensors block 550, sensors, e.g. the sensors 210 described above, are configured to measure pressure, e.g. PEEP, oxygen saturation of the user and the partial pressure of arterial blood. As illustrated in FIG. 5, these sensor measurements 530 are provided to the controller 130 at control block 520, and the controller 130 controls the operation of ventilator system 100 as described above, e.g. by generating the output control parameters 540. As illustrated in FIG. 5, the control block 520 and sensors block 550 and the connections between the two are configured to form a feedback loop which enables the operation of the ventilator system 100 to be monitored and controlled in order to maintain the sensor measurements 530 at desired values and/or within desired ranges, based on the target values 510. In particular, the controller 130 may be configured, in the control block 520, to generate the output control values so that the ventilators system is operated to maintain a difference between a determined PEEP and the target PEEP value 512 is less than a predetermined threshold, such that a determined oxygen saturation is greater than or equal to a target oxygen saturation value 514 and/or such that a determined partial pressure of carbon dioxide within arterial blood of the user is less than or equal to a target partial pressure value 516.

Figures 6A, 6B, 6C, 6D, 6E:
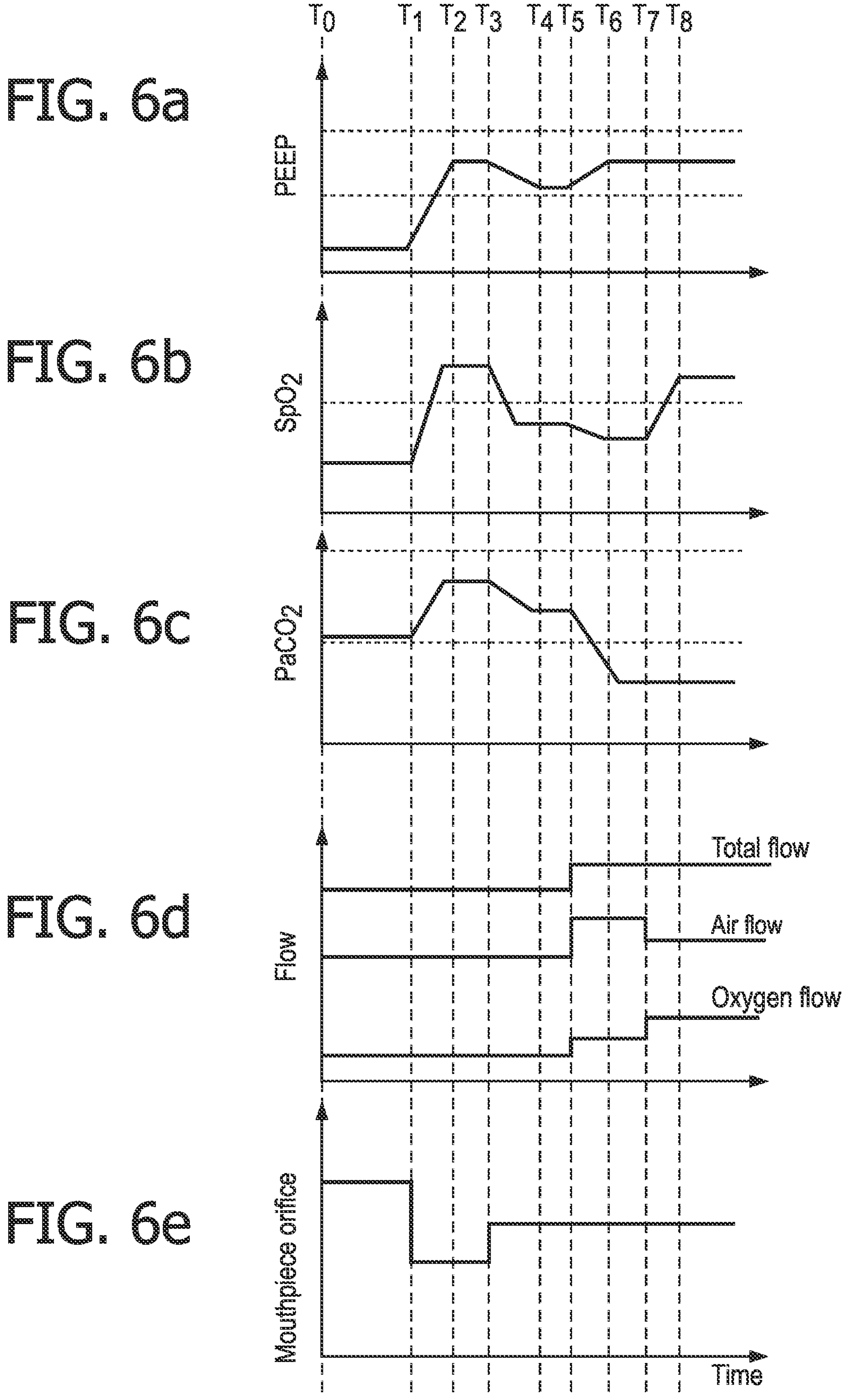
FIGS. 6*a* to 6*e* are graphs illustrating an example variation in parameters relating to the ventilator system during operation according to the methods illustrated in FIGS. 4 and 5.

FIGS. 6*a* to 6*e*, collectively referred to as FIG. 6, illustrate example variations of values of PEEP, oxygen saturation, partial pressure of carbon dioxide, total flow rate of air and oxygen supplied via the nasal cannula and orifice area, e.g. flow area of the passage 202, respectively during operation of the ventilator system 100, e.g. according to the method illustrated in FIGS. 4 and 5.

As illustrated in FIG. 6, at time $T_0$ a measured value of pressure e.g. PEEP, may be outside of, e.g. below, a desirable pressure range, a measured value of oxygen saturation may be less than the target oxygen saturation value 514 and a measured value of partial pressure of carbon dioxide may be greater than the target partial pressure value 516.

At time $T_1$, the controller 130 controls the operation of the ventilator system 100 to reduce a flow area of the passage 202 in the mouthpiece and accordingly, between $T_1$ and $T_2$, the pressure measurement increases to within the desirable pressure range and the measured oxygen saturation increased to a value greater than the target oxygen saturation value 514. However, the partial pressure of carbon dioxide does remains greater than the target partial pressure value 516.

In response measurement from the sensors, at time $T_3$, the controller 130 controls the operation of the ventilator system 100 to increase the flow area of the passage 202 in the mouthpiece and accordingly, between $T_3$ and $T_4$, the pressure measurement, the measured oxygen saturation value and the partial pressure of carbon dioxide reduce. As depicted, the value of pressure may be within the desirable range. However, the value of oxygen saturation and partial pressure of carbon dioxide may be below and above the corresponding target values respectively.

In response to measurement from the sensors, at time $T_5$, the controller 130 controls the operation of the ventilator system 100 to increase a flow rate of oxygen supplied through the nasal cannula and a total flow rate of air and oxygen supplied though the nasal cannula. Accordingly, between $T_5$ and $T_6$, the pressure measurement increases, remaining within the desirable pressure range, and the partial pressure of carbon dioxide reduces to below the target partial pressure value 516. However, the measured oxygen saturation reduced further to a value less than the target oxygen saturation value 514.

In response to the measurements from the sensors, at time $T_7$, the controller 130 controls the operation of the ventilator system 100 to further increase the flow rate of oxygen supplied through the nasal cannula without changing the total flow rate of air and oxygen supplied through the nasal cannula, thereby increasing a concentration of oxygen supplied through the nasal cannula. Accordingly, between times $T_7$ and $T_8$, the pressure measurement and partial pressure of carbon dioxide remain constant and the oxygen saturation value increases to above the target oxygen saturation value 514. At time $T_8$ the values of pressure, e.g. PEEP, oxygen saturation and partial pressure of carbon dioxide are within the respective desirable ranges. Hence, the controller may continue operating the ventilator system 100 in this way and monitoring the values determined by the sensors until the measured values change.

In the example described above, the controller 130 is configured to control the flow area of the passage 202 in the mouthpiece, e.g. in order increase the pressure value and/or the oxygen saturation value, before controlling the flow rate of oxygen supplied through the nasal cannula and a total flow rate of air and oxygen supplied though the nasal cannula. However, in other arrangements, the controller may control the operation of the ventilator system differently, e.g. by changing the output control parameters from the controller in a different order and/or by changing two or more of the output control parameters simultaneously or substantially simultaneously.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A ventilator system comprising:

a nasal cannula configured for supplying a flow of air and/or oxygen to one or both nares of the user;

an air and oxygen supplying apparatus configured to supply flows of air and oxygen to the nasal cannula;

a mouthpiece configured to be received within a user's mouth, wherein the mouthpiece comprises:

a passage for permitting a flow of gases through the mouthpiece between a first side of the passage configured to be inside the user's mouth and a second side of the passage configured to be outside the user's mouth;

a passage adjustment component for selectively adjusting a flow area of the passage; and one or more sensors mounted on the mouthpiece, wherein the sensors comprise a pressure sensor configured to measure a pressure at the first side of the passage; and a controller configured to control, based on the pressure measured by the pressure sensor:

a flow rate and/or concentration of oxygen supplied to the user through a nasal cannula;

a total flow rate of air and oxygen supplied through the nasal cannula; and the flow area of the passage.

2. The ventilator system of claim 1, wherein the controller is configured to determine a Positive End-Expiratory Pressure, PEEP, based on one or more pressure measurements from the pressure sensor; and wherein the controller is configured to control, based on the determined PEEP:

the flow rate and/or concentration of oxygen supplied through the nasal cannula;

the total flow rate of air and oxygen supplied through the nasal cannula; and the flow area of the passage.

3. The ventilator system of claim 1, wherein the system further comprises an oxygen saturation sensor configured to determine oxygen saturation of the user, wherein the controller is configured to control, based on the measured oxygen saturation:

the flow rate and/or concentration of oxygen supplied through the nasal cannula;

the total flow rate of air and oxygen supplied through the nasal cannula; and the flow area of the passage.

4. The ventilator system of claim 3, wherein the oxygen saturation sensor is mounted on the mouthpiece.

5. The ventilator system of claim 1 wherein the sensors comprise a temperature sensor configured to measure a temperature of gases passing through the passage.

6. The ventilator system of claim 5, wherein the controller is configured to control, based on the measured temperature:

a flow rate and/or concentration of oxygen supplied through the nasal cannula;

a total flow rate of air and oxygen supplied through the nasal cannula; and the flow area of the passage.

7. The ventilator system of claim 1, wherein the sensors comprise a capnogram configured to measure a partial pressure of carbon dioxide in gases passing through the passage.

8. The ventilator system of claim 7, wherein the controller is configured to determine an end tidal carbon dioxide measurement based on measurements from the capnogram.

9. The ventilator system of claim 7, wherein the controller is configured to control, based on the measurement from the capnogram:

a flow rate and/or concentration of oxygen supplied through the nasal cannula;

a total flow rate of air and oxygen supplied through the nasal cannula; and the flow area of the passage.

10. The ventilator system of claim 7, wherein the controller is configured to determine a partial pressure of carbon dioxide within arterial blood of the user based on measurements from the capnogram, and wherein the controller is configured to control, based on the determined partial pressure of carbon dioxide within the arterial blood of the user:

a flow rate and/or concentration of oxygen supplied through the nasal cannula;

a total flow rate of air and oxygen supplied through the nasal cannula; and the flow area of the passage.

11. The ventilator system of claim 1, wherein the system comprises a user input device, wherein the controller is configured to receive one or more input control parameters from the user or another user via the user input device; and control, based on the one or more input control parameters:

a flow rate and/or concentration of oxygen supplied through the nasal cannula;

a total flow rate of air and oxygen supplied through the nasal cannula; and the flow area of the passage, wherein the input control parameters comprise: a target pressure value, a target oxygen saturation value and/or a target value of partial pressure of carbon.

12. The ventilator system of claim 1, wherein the controller is configured to monitor measurements from the one or more sensors mounted on the mouthpiece and control:

a flow rate and/or concentration of oxygen supplied through the nasal cannula;

a total flow rate of air and oxygen supplied through the nasal cannula; and the flow area of the passage, in order to maintain determined values of pressure, oxygen saturation and/or partial pressure of carbon dioxide within respective desirable ranges, the desirable ranges determined based on respective target values defined by the input control parameters.

13. A method of operating a ventilator system, wherein the ventilator system comprises:

a nasal cannula configured for supplying a flow of air and/or oxygen to one or both nares of a user;

an air and oxygen supplying apparatus configured to supply flows of air and oxygen to the nasal cannula;

a mouthpiece configured to be received within the user's mouth, wherein the mouthpiece comprises:

a passage for permitting a flow of gases through the mouthpiece between a first side of the passage configured to be inside the user's mouth and a second side of the passage configured to be outside the user's mouth;

a passage adjustment component for selectively adjusting a flow area of the passage; and one or more sensors mounted on the mouthpiece, wherein the sensors comprise a pressure sensor configured to measure a pressure at the first side of the passage; and a controller configured to control the operation of the ventilator system, wherein the method comprises:

determining a pressure measurement from the pressure sensor; and, based on the determined pressure measurement:

controlling a flow rate and/or concentration of oxygen supplied through the nasal cannula;

controlling a total flow rate of air and oxygen supplied through the nasal cannula; and controlling the flow area of the passage.

* * * * *